(12) United States Patent
Bosserhoff et al.

(10) Patent No.: US 8,148,493 B2
(45) Date of Patent: Apr. 3, 2012

(54) METHOD FOR INHIBITING "MELANOMA INHIBITORY ACTIVITY" MIA

(75) Inventors: Anja-Katrin Bosserhoff, Regensburg (DE); Reinhard Buettner, Wachtberg/Pech (DE); Mara Szyrach, Rottenburg (DE); Guenter Auerbach, Lappersdorf (DE); Piotr Jachimczak, Wuerzburg (DE); Karl-Hermann Schlingensiepen, Donaustauf (DE)

(73) Assignee: Antisense Pharma GmbH, Regensburg (DE)

( * ) Notice: Subject to any disclaimer, the term of this patent is extended or adjusted under 35 U.S.C. 154(b) by 614 days.

(21) Appl. No.: 12/289,153

(22) Filed: Oct. 21, 2008

(65) Prior Publication Data

US 2010/0273705 A1   Oct. 28, 2010

Related U.S. Application Data

(63) Continuation of application No. 10/502,771, filed as application No. PCT/EP02/00893 on Jan. 29, 2002, now abandoned.

(51) Int. Cl.
*A61K 38/04* (2006.01)
(52) U.S. Cl. ....................................................... 530/327
(58) Field of Classification Search ................... 530/327
See application file for complete search history.

(56) References Cited

FOREIGN PATENT DOCUMENTS

| EP | 1 133 994 A | 9/2001 |
|----|----|----|
| JP | 10-226700 | 8/1998 |
| JP | 2002-293794 A | 9/2002 |
| JP | 2002293794 A * | 10/2002 |
| WO | WO 01/78655 A2 | 10/2001 |

OTHER PUBLICATIONS

Hau et al (J. Invest. Derm., 119:562-569, 2002).*
Lougheed et al (PNAS, 98:5515-5520, 2001).*
Burgess et al. (J. Cell Bio., 111:2129-2138, 1990).*
Lazar et al. (Mol. Cell. Bio., 8:1247-1252, 1988).*
Schumacher et al (Science, 271:1854-1857, 1996).*
Bissantz et al. (Proteins. Jan. 1, 2003; 50 (1): 5-25).*
Gura (Science. 1997; 278: 1041-1042).*
Kelland (Eur. J. Cancer. Apr. 2004; 40 (6): 827-836).*
Stephen et al (J. Mol. Biol., 248:58-78, 1995).*
Holmes (Expert Opinion on Investigational Drugs 2001; 10: 511-519).*
Tame (J. Comput. Aided Mol. Des. Mar. 1999; 13 (2): 99-108).*
Dixon (Proteins. 1997; Suppl 1: 198-204).*
Lensink et al. (Proteins. 2007; 69: 704-718).*
Burrows et al. "Fine mapping of inhibitory anti-α5 monoclonal antibody epitopes that differentially affect integrin-ligand binding" Biochem. J. vol. 344 (1999), pp. 527-533.
Miyake et al. "A specific cell surface glycoconjugate cell motility: Evidence by functional monoclonal antibodies that inhibit cell motility and tumor cell metastasis." Biochemistry vol. 30,(1991), pp. 3328-3334.
Stoll et al. "The extracellular human melanoma inhibitory activity (MIA) protein adopts an SH3 domain-like fold." The Embo Journal 20:3 (2001), 340-349.

* cited by examiner

*Primary Examiner* — Misook Yu
*Assistant Examiner* — Brad Duffy
(74) *Attorney, Agent, or Firm* — Jacobson Holman PLLC (57) ABSTRACT

The present invention is directed to peptides, antibodies and antibody fragments inhibiting activity of "Melanoma Inhibitory Activity" (MIA).

10 Claims, 1 Drawing Sheet

SEQUENCE LISTING

```
<160> NUMBER OF SEQ ID NOS: 57

<210> SEQ ID NO 1
<211> LENGTH: 7
<212> TYPE: PRT
<213> ORGANISM: artificial sequence
<220> FEATURE:
<223> OTHER INFORMATION: from phage display screening

<400> SEQUENCE: 1

Val Pro His Ile Pro Pro Asn
1               5

<210> SEQ ID NO 2
<211> LENGTH: 7
<212> TYPE: PRT
<213> ORGANISM: artificial sequence
<220> FEATURE:
<223> OTHER INFORMATION: from phage display screening

<400> SEQUENCE: 2

Met Pro Pro Thr Gln Val Ser
1               5

<210> SEQ ID NO 3
<211> LENGTH: 7
<212> TYPE: PRT
<213> ORGANISM: artificial sequence
<220> FEATURE:
<223> OTHER INFORMATION: from phage display screening

<400> SEQUENCE: 3

Gln Met His Pro Trp Pro Pro
1               5

<210> SEQ ID NO 4
<211> LENGTH: 7
<212> TYPE: PRT
<213> ORGANISM: artificial sequence
<220> FEATURE:
<223> OTHER INFORMATION: from phage display screening

<400> SEQUENCE: 4

Gln Pro Pro Phe Trp Gln Phe
1               5

<210> SEQ ID NO 5
<211> LENGTH: 7
<212> TYPE: PRT
<213> ORGANISM: artificial sequence
<220> FEATURE:
<223> OTHER INFORMATION: from phage display screening

<400> SEQUENCE: 5

Thr Pro Pro Gln Gly Leu Ala
1               5

<210> SEQ ID NO 6
<211> LENGTH: 7
<212> TYPE: PRT
<213> ORGANISM: artificial sequence
<220> FEATURE:
```

<223> OTHER INFORMATION: from phage display screening

<400> SEQUENCE: 6

Ile Pro Pro Tyr Asn Thr Leu
1               5

<210> SEQ ID NO 7
<211> LENGTH: 7
<212> TYPE: PRT
<213> ORGANISM: artificial sequence
<220> FEATURE:
<223> OTHER INFORMATION: from phage display screening

<400> SEQUENCE: 7

Ala Val Arg Pro Ala Pro Leu
1               5

<210> SEQ ID NO 8
<211> LENGTH: 7
<212> TYPE: PRT
<213> ORGANISM: artificial sequence
<220> FEATURE:
<223> OTHER INFORMATION: from phage display screening

<400> SEQUENCE: 8

Gly Ala Lys Pro His Pro Gln
1               5

<210> SEQ ID NO 9
<211> LENGTH: 7
<212> TYPE: PRT
<213> ORGANISM: artificial sequence
<220> FEATURE:
<223> OTHER INFORMATION: from phage display screening

<400> SEQUENCE: 9

Gln Gln Leu Ser Pro Leu Pro
1               5

<210> SEQ ID NO 10
<211> LENGTH: 7
<212> TYPE: PRT
<213> ORGANISM: artificial sequence
<220> FEATURE:
<223> OTHER INFORMATION: from phage display screening

<400> SEQUENCE: 10

Gly Pro Pro Pro Ser Pro Val
1               5

<210> SEQ ID NO 11
<211> LENGTH: 7
<212> TYPE: PRT
<213> ORGANISM: artificial sequence
<220> FEATURE:
<223> OTHER INFORMATION: from phage display screening

<400> SEQUENCE: 11

Leu Pro Leu Thr Pro Leu Pro
1               5

<210> SEQ ID NO 12
<211> LENGTH: 12
<212> TYPE: PRT
<213> ORGANISM: artificial sequence
<220> FEATURE:
<223> OTHER INFORMATION: from phage display screening

```
<400> SEQUENCE: 12

Gln Leu Asn Val Asn His Gln Ala Arg Ala Asp Gln
1               5                   10

<210> SEQ ID NO 13
<211> LENGTH: 12
<212> TYPE: PRT
<213> ORGANISM: artificial sequence
<220> FEATURE:
<223> OTHER INFORMATION: from phage display screening

<400> SEQUENCE: 13

Thr Ser Ala Ser Thr Arg Pro Glu Leu His Tyr Pro
1               5                   10

<210> SEQ ID NO 14
<211> LENGTH: 12
<212> TYPE: PRT
<213> ORGANISM: artificial sequence
<220> FEATURE:
<223> OTHER INFORMATION: from phage display screening#

<400> SEQUENCE: 14

Thr Phe Leu Pro His Gln Met His Pro Trp Pro Pro
1               5                   10

<210> SEQ ID NO 15
<211> LENGTH: 12
<212> TYPE: PRT
<213> ORGANISM: artificial sequence
<220> FEATURE:
<223> OTHER INFORMATION: from phage display screening

<400> SEQUENCE: 15

Val Pro His Ile Pro Pro Asn Ser Met Ala Leu Thr
1               5                   10

<210> SEQ ID NO 16
<211> LENGTH: 12
<212> TYPE: PRT
<213> ORGANISM: artificial sequence
<220> FEATURE:
<223> OTHER INFORMATION: from phage display screening

<400> SEQUENCE: 16

Arg Leu Thr Leu Leu Val Leu Ile Met Pro Ala Pro
1               5                   10

<210> SEQ ID NO 17
<211> LENGTH: 9
<212> TYPE: PRT
<213> ORGANISM: artificial sequence
<220> FEATURE:
<223> OTHER INFORMATION: from phage display screening

<400> SEQUENCE: 17

Arg Lys Leu Pro Pro Arg Pro Arg Arg
1               5

<210> SEQ ID NO 18
<211> LENGTH: 12
<212> TYPE: PRT
<213> ORGANISM: artificial sequence
<220> FEATURE:
<223> OTHER INFORMATION: from phage display screening

<400> SEQUENCE: 18
```

-continued

Val Leu Ala Ser Gln Ile Ala Thr Thr Pro Ser Pro
1               5                   10

<210> SEQ ID NO 19
<211> LENGTH: 12
<212> TYPE: PRT
<213> ORGANISM: artificial sequence
<220> FEATURE:
<223> OTHER INFORMATION: from phage display screening

<400> SEQUENCE: 19

Thr Pro Leu Thr Lys Leu Pro Ser Val Asn His Pro
1               5                   10

<210> SEQ ID NO 20
<211> LENGTH: 13
<212> TYPE: PRT
<213> ORGANISM: artificial sequence
<220> FEATURE:
<223> OTHER INFORMATION: from phage display screening

<400> SEQUENCE: 20

Pro Pro Asn Ser Phe Ser Ser Ala Gly Gly Gln Arg Thr
1               5                   10

<210> SEQ ID NO 21
<211> LENGTH: 15
<212> TYPE: PRT
<213> ORGANISM: artificial sequence
<220> FEATURE:
<223> OTHER INFORMATION: from phage display screening

<400> SEQUENCE: 21

Glu Gln Asp Ser Arg Gln Gly Gln Glu Leu Thr Lys Lys Gly Leu
1               5                   10                  15

<210> SEQ ID NO 22
<211> LENGTH: 13
<212> TYPE: PRT
<213> ORGANISM: artificial sequence
<220> FEATURE:
<223> OTHER INFORMATION: from phage display screening

<400> SEQUENCE: 22

Glu Thr Thr Ile Val Ile Thr Trp Thr Pro Ala Pro Arg
1               5                   10

<210> SEQ ID NO 23
<211> LENGTH: 13
<212> TYPE: PRT
<213> ORGANISM: artificial sequence
<220> FEATURE:
<223> OTHER INFORMATION: from phage display screening

<400> SEQUENCE: 23

Thr Ser Leu Leu Ile Ser Trp Asp Ala Pro Ala Val Thr
1               5                   10

<210> SEQ ID NO 24
<211> LENGTH: 13
<212> TYPE: PRT
<213> ORGANISM: artificial sequence
<220> FEATURE:
<223> OTHER INFORMATION: from phage display screening

<400> SEQUENCE: 24

Asn Ser Leu Leu Val Ser Trp Gln Pro Pro Arg Ala Arg
1               5                   10

<210> SEQ ID NO 25
<211> LENGTH: 12
<212> TYPE: PRT
<213> ORGANISM: artificial sequence
<220> FEATURE:
<223> OTHER INFORMATION: from phage display screening

<400> SEQUENCE: 25

Tyr Asn Leu Pro Lys Val Ser Ser Asn Leu Ser Pro
1               5                   10

<210> SEQ ID NO 26
<211> LENGTH: 12
<212> TYPE: PRT
<213> ORGANISM: artificial sequence
<220> FEATURE:
<223> OTHER INFORMATION: from phage display screening

<400> SEQUENCE: 26

Met Pro Pro Thr Gln Val Ser Lys Phe Arg Leu Ile
1               5                   10

<210> SEQ ID NO 27
<211> LENGTH: 12
<212> TYPE: PRT
<213> ORGANISM: artificial sequence
<220> FEATURE:
<223> OTHER INFORMATION: from phage display screening

<400> SEQUENCE: 27

Ala Asn Ile Asp Ala Thr Pro Leu Phe Leu Arg Ala
1               5                   10

<210> SEQ ID NO 28
<211> LENGTH: 12
<212> TYPE: PRT
<213> ORGANISM: artificial sequence
<220> FEATURE:
<223> OTHER INFORMATION: from phage display screening

<400> SEQUENCE: 28

Leu Leu Arg Thr Thr Glu Thr Leu Pro Met Phe Leu
1               5                   10

<210> SEQ ID NO 29
<211> LENGTH: 7
<212> TYPE: PRT
<213> ORGANISM: artificial sequence
<220> FEATURE:
<223> OTHER INFORMATION: from phage display screening

<400> SEQUENCE: 29

Ser Ala Leu Glu Pro Leu Val
1               5

<210> SEQ ID NO 30
<211> LENGTH: 7
<212> TYPE: PRT
<213> ORGANISM: artificial sequence
<220> FEATURE:
<223> OTHER INFORMATION: from phage display screening

<400> SEQUENCE: 30

Gly Ser Pro Thr Pro Asn Ala
1               5

```
<210> SEQ ID NO 31
<211> LENGTH: 7
<212> TYPE: PRT
<213> ORGANISM: artificial sequence
<220> FEATURE:
<223> OTHER INFORMATION: from phage display screening

<400> SEQUENCE: 31

Ala Pro Ser His Ala Thr His
1               5

<210> SEQ ID NO 32
<211> LENGTH: 7
<212> TYPE: PRT
<213> ORGANISM: artificial sequence
<220> FEATURE:
<223> OTHER INFORMATION: from phage display screening

<400> SEQUENCE: 32

Thr Thr Val Gly His Ser Asp
1               5

<210> SEQ ID NO 33
<211> LENGTH: 7
<212> TYPE: PRT
<213> ORGANISM: artificial sequence
<220> FEATURE:
<223> OTHER INFORMATION: from phage display screening

<400> SEQUENCE: 33

Thr His Phe Ser Thr Phe Thr
1               5

<210> SEQ ID NO 34
<211> LENGTH: 7
<212> TYPE: PRT
<213> ORGANISM: artificial sequence
<220> FEATURE:
<223> OTHER INFORMATION: from phage display screening

<400> SEQUENCE: 34

Ser Leu Leu Leu Asp Thr Ser
1               5

<210> SEQ ID NO 35
<211> LENGTH: 12
<212> TYPE: PRT
<213> ORGANISM: artificial sequence
<220> FEATURE:
<223> OTHER INFORMATION: from phage display screening

<400> SEQUENCE: 35

Ser Val Ala Met Lys Ala His Lys Pro Leu Leu Pro
1               5                   10

<210> SEQ ID NO 36
<211> LENGTH: 12
<212> TYPE: PRT
<213> ORGANISM: artificial sequence
<220> FEATURE:
<223> OTHER INFORMATION: from phage display screening

<400> SEQUENCE: 36

Asn Thr Ile Pro Gly Phe Ala Ser Lys Ser Leu Asp
1               5                   10

<210> SEQ ID NO 37
<211> LENGTH: 12
```

```
<212> TYPE: PRT
<213> ORGANISM: artificial sequence
<220> FEATURE:
<223> OTHER INFORMATION: from phage display screening

<400> SEQUENCE: 37

Val Ser Asn Tyr Lys Phe Tyr Ser Thr Thr Ser Ser
1               5                   10

<210> SEQ ID NO 38
<211> LENGTH: 12
<212> TYPE: PRT
<213> ORGANISM: artificial sequence
<220> FEATURE:
<223> OTHER INFORMATION: from phage display screening

<400> SEQUENCE: 38

Val Ser Arg His Gln Ser Trp His Pro His Asp Leu
1               5                   10

<210> SEQ ID NO 39
<211> LENGTH: 12
<212> TYPE: PRT
<213> ORGANISM: artificial sequence
<220> FEATURE:
<223> OTHER INFORMATION: from phage display screening

<400> SEQUENCE: 39

His Leu Asn Ile Leu Ser Thr Leu Trp Lys Tyr Arg
1               5                   10

<210> SEQ ID NO 40
<211> LENGTH: 12
<212> TYPE: PRT
<213> ORGANISM: artificial sequence
<220> FEATURE:
<223> OTHER INFORMATION: from phage display screening

<400> SEQUENCE: 40

His Asn Ala Ser Pro Ser Trp Gly Ser Pro Val Met
1               5                   10

<210> SEQ ID NO 41
<211> LENGTH: 12
<212> TYPE: PRT
<213> ORGANISM: artificial sequence
<220> FEATURE:
<223> OTHER INFORMATION: from phage display screening

<400> SEQUENCE: 41

Ser His Pro Trp Asn Ala Gln Arg Glu Leu Ser Val
1               5                   10

<210> SEQ ID NO 42
<211> LENGTH: 12
<212> TYPE: PRT
<213> ORGANISM: artificial sequence
<220> FEATURE:
<223> OTHER INFORMATION: from phage display screening

<400> SEQUENCE: 42

His His Trp Pro Phe Trp Arg Thr Leu Pro Leu Ser
1               5                   10

<210> SEQ ID NO 43
<211> LENGTH: 12
<212> TYPE: PRT
<213> ORGANISM: artificial sequence
```

```
<220> FEATURE:
<223> OTHER INFORMATION: from phage display screening

<400> SEQUENCE: 43

Trp His Thr Lys Phe Leu Pro Arg Tyr Leu Pro Ser
1               5                   10

<210> SEQ ID NO 44
<211> LENGTH: 12
<212> TYPE: PRT
<213> ORGANISM: artificial sequence
<220> FEATURE:
<223> OTHER INFORMATION: from phage display screening

<400> SEQUENCE: 44

Asn Asn Thr Ser Phe Thr Val Val Pro Ser Val Pro
1               5                   10

<210> SEQ ID NO 45
<211> LENGTH: 12
<212> TYPE: PRT
<213> ORGANISM: artificial sequence
<220> FEATURE:
<223> OTHER INFORMATION: from phage display screening

<400> SEQUENCE: 45

Ser His Leu Ser Thr Trp Lys Trp Trp Gln Asn Arg
1               5                   10

<210> SEQ ID NO 46
<211> LENGTH: 12
<212> TYPE: PRT
<213> ORGANISM: artificial sequence
<220> FEATURE:
<223> OTHER INFORMATION: from phage display screening

<400> SEQUENCE: 46

Phe His Trp His Pro Arg Leu Trp Pro Leu Pro Ser
1               5                   10

<210> SEQ ID NO 47
<211> LENGTH: 12
<212> TYPE: PRT
<213> ORGANISM: artificial sequence
<220> FEATURE:
<223> OTHER INFORMATION: from phage display screening

<400> SEQUENCE: 47

Trp His Trp Thr Tyr Gly Trp Arg Pro Pro Ala Met
1               5                   10

<210> SEQ ID NO 48
<211> LENGTH: 12
<212> TYPE: PRT
<213> ORGANISM: artificial sequence
<220> FEATURE:
<223> OTHER INFORMATION: from phage display screening

<400> SEQUENCE: 48

Phe His Trp Arg Tyr Pro Leu Pro Leu Pro Gly Gln
1               5                   10

<210> SEQ ID NO 49
<211> LENGTH: 12
<212> TYPE: PRT
<213> ORGANISM: artificial sequence
<220> FEATURE:
<223> OTHER INFORMATION: from phage display screening
```

-continued

```
<400> SEQUENCE: 49

Trp His Trp Pro Leu Phe Ile Pro Asn Thr Thr Ala
1               5                   10

<210> SEQ ID NO 50
<211> LENGTH: 12
<212> TYPE: PRT
<213> ORGANISM: artificial sequence
<220> FEATURE:
<223> OTHER INFORMATION: from phage display screening

<400> SEQUENCE: 50

Trp His Asn Gly Ile Trp Trp His Tyr Gly Val Arg
1               5                   10

<210> SEQ ID NO 51
<211> LENGTH: 12
<212> TYPE: PRT
<213> ORGANISM: artificial sequence
<220> FEATURE:
<223> OTHER INFORMATION: from phage display screening

<400> SEQUENCE: 51

His His Leu Asn Tyr Leu Trp Pro Trp Thr Arg Val
1               5                   10

<210> SEQ ID NO 52
<211> LENGTH: 12
<212> TYPE: PRT
<213> ORGANISM: artificial sequence
<220> FEATURE:
<223> OTHER INFORMATION: from phage display screening

<400> SEQUENCE: 52

Phe Trp His Arg Trp Ser Thr Phe Pro Glu Gln Pro
1               5                   10

<210> SEQ ID NO 53
<211> LENGTH: 12
<212> TYPE: PRT
<213> ORGANISM: artificial sequence
<220> FEATURE:
<223> OTHER INFORMATION: from phage display screening

<400> SEQUENCE: 53

Trp His Met Ser Tyr Phe Trp Thr Arg Pro Pro Gln
1               5                   10

<210> SEQ ID NO 54
<211> LENGTH: 12
<212> TYPE: PRT
<213> ORGANISM: artificial sequence
<220> FEATURE:
<223> OTHER INFORMATION: from phage display screening

<400> SEQUENCE: 54

Phe His Leu Asn Trp Pro Ser Arg Ala Asp Tyr Leu
1               5                   10

<210> SEQ ID NO 55
<211> LENGTH: 12
<212> TYPE: PRT
<213> ORGANISM: artificial sequence
<220> FEATURE:
<223> OTHER INFORMATION: from phage display screening

<400> SEQUENCE: 55
```

```
Trp His Lys Asn Thr Asn Trp Pro Trp Arg Thr Leu
1               5                   10

<210> SEQ ID NO 56
<211> LENGTH: 12
<212> TYPE: PRT
<213> ORGANISM: artificial sequence
<220> FEATURE:
<223> OTHER INFORMATION: from phage display screening

<400> SEQUENCE: 56

Ala Leu Ser Pro Ser Gln Ser His Pro Val Arg Ser
1               5                   10

<210> SEQ ID NO 57
<211> LENGTH: 12
<212> TYPE: PRT
<213> ORGANISM: artificial sequence
<220> FEATURE:
<223> OTHER INFORMATION: from phage display screening

<400> SEQUENCE: 57

Gly Thr Gln Ser Thr Ala Ile Pro Ala Pro Thr Asp
1               5                   10
```

METHOD FOR INHIBITING "MELANOMA INHIBITORY ACTIVITY" MIA

This is a continuation of Ser. No. 10/502,771, now abandoned, filed Mar. 11, 2005, which is a 371 of PCT/EP02/00893, filed Jan. 29, 2002.

FIELD OF THE INVENTION

The present invention pertains to peptides and antibodies inhibiting activity of "Melanoma Inhibitory Activity" MIA.

BACKGROUND AND PRIOR ART

The polypeptide "Melanoma Inhibitory Activity" MIA, was discovered in 1989 as a factor that inhibits growth of melanoma tumor cells. The melanoma inhibitory activity (MIA) protein was identified within growth-inhibiting activities purified from tissue culture supernatant of the human melanoma cell line HTZ-19 (Bogdahn et al., Cancer Res. 1989; 49: 5358-5363). The antiproliferative action of MIA was also demonstrated in other tumor cells and Peripheral Blood Mononuclear Cells (Jachimczak et al., 2000, Proceeding of AACR, 41: 115).

Furthermore, in situ-hybridization experiments, as well as immuno histochemistry localize MIA in the developmental embryo within the growth zone of the skeletal system, and it is being expressed, secreted, and deposited around the chondrocytes.

In the developing mouse the expression is correlated with the forming of the skeletal system and is postnatal fading out with the exception of being expressed again during the maturation of the mammary system.

However, in the case of the tumors, MIA was found to be expressed and secreted into the serum by all of the malignant melanomas examined, but not in other skin tumor, including basal cell cancer and squamous cell cancer, nor in normal melanocytes and keratinocytes.

"Melanoma Inhibitory Activity", MIA, is translated as a 131 amino acid precursor molecule and processed into a mature 107 amino acid protein after cleavage of a secretion signal. MIA provides clinically useful parameters in patients with Metastatic melanoma stages III and IV (Bosserhoff et al., Cancer Res. 1997; 57: 3149-3153; Bosserhoff et al., Hautarzt. 1998; 49: 762-769; Dreau et al., Oncol. Res. 1999; 11: 55-61; Deichmann et al., J. Clin. Oncol. 999; 17: 1891-1896). MIA was described to elicit antitumor activity by inhibiting proliferation of melanoma cell lines in vitro (Blesch et al., Cancer Res. 1994; 54: 5695-5701; Bogdahn et al., Cancer Res. 1989; 49: 5358-5363). However, further studies have revealed expression patterns inconsistent with a tumor suppressor. Expression of the wild-type MIA protein gene was not detected in normal skin and melanocytes, but was associated with progression of melanocytic tumors (Bosserhoff et al., Cancer Res. 1997; 57: 3149-3153; van Groningen et al., Cancer Res. 1995; 55: 6237-6243). More recently, it was suggested that the MIA protein specifically inhibits attachment of melanoma cells to fibronectin and laminin, thereby masking the binding site of integrins to these extracellular matrix (ECM) components and promoting invasion and metastasis in vivo (Bosserhoff et al., Cancer Res. 1997; 57: 3149-3153; Bosserhoff et al., J. Pathol. 1999; 187: 446-454; Guba et al., Br. J. Cancer 2000; 83: 1216-1222). Thus, the growth-inhibitory activity in vitro reflects the ability of the protein to interfere with the attachment of cell lines to the surface of tissue culture dishes in vitro (Blesch et al., Cancer Res. 1994; 54: 5695-5701).

Weilbach et al. (1990 Cancer Res. 50; 6981-86) further demonstrated that MIA inhibits cell proliferation by prolonging of the S-Phase and arrest of the cells in the G2 compartment.

Human rMIA inhibits IL-2- or PHA-induced Peripheral Blood Mononuclear Cells (PBMCs) proliferation in a dose-dependant manner. Additionally, auto- and allogenic LAK-cytotoxicity has been inhibited by MIA (Jachimczak et al., 2000, Proceeding of AACR, 41: 115).

Blesch et al. (1994 Cancer Res. 54; 5695-5701) confirmed that MIA acts as a potent tumor cell growth inhibitor for malignant melanoma cell and further extended this observation to other neuroectodermal tumors and concluded that MIA might be attractive as a future antitumor therapeutical substance.

The clinical correlation of MIA expression with melanoma progression was discovered by Bosserhoff et al. (1997, Cancer Res. 57; 3149-53; 1997, Anti-cancer Res. 19; 2691-3) showing enhanced MIA levels in 13-23% of stage I and II melanomas, but in 100% of stage III or stage IV disease.

Van Groningen et al. (1995 Cancer Res. 55; 6237-43) found MIA mRNA expression in non metastasising cell lines and an inverse correlation of MIA mRNA expression with pigmentation in melanoma metastasis lesions.

The 3D structure of the recombinant human MIA in solution was determined recently by multidimensional NMR spectroscopy and revealed that MIA is the first extracellular protein known to adopt an SH3 domain like-fold. These studies also provided evidence of specific interaction between a binding fold of MIA and a partial fibronectin peptide that has been implicated in integrin binding. It appears that MIA belongs to a growing family of proteins that promote invasion and metastasis by inhibiting specific interactions between integrins and ECM molecules within the local tumor milieu.

Furthermore, the 1.4 Angstrom resolution crystal structure of human MIA protein was determined by X-ray protein crystallography using multi-wavelength anomalous diffraction (MAD) (Lougheed et al., PNAS 2001 May 8; 98 (10): 5515-5520). The structure confirms a conventional SH3-like fold of MIA.

The idea that proline-rich peptides are ligands of the SH3 domains has been supported by a number of experiments (for example see Ren et al., Science 259, 1157-1161, 1993; Gout et al., Cell 75, 25-26, 1993). Yu and coworkers (Cell 76, 933-945, 1994) have proposed that the specificity of SH3-ligand interactions may arise from the reciprocal recognition of non-proline peptide residues with non-conserved protein side chains. Musacchio et al. (Nat. Struct. Biol 1(8), 546-551, 1994) were unable to identify such specific interactions in complexes of SH3-domain proteins.

Lougheed et al. (PNAS 2001 May 8; 98 (10):5515-5520) tested the ability of MIA to bind proline-rich peptides by using phase display, but were unable to identify significant peptide binders out of a biased polyproline helix phage display library.

In contrast to these data the invention described below is based mainly on ligands with a high content of proline that do not possess a consensus sequence motif for binding to SH3 domains.

SUMMARY OF THE INVENTION

One embodiment of the invention is a peptide inhibiting activity of "Melanoma Inhibitory Activity" (MIA) selected from the group consisting of peptides with the sequence SEQ ID No. 1 to 57.

These peptides preferably inhibit MIA by binding to MIA.

In a preferred embodiment the peptide contains a high proline content according to SEQUENCE LISTING GROUP: A and/or a high content of Trp, His, Tyr according to SEQUENCE LISTING GROUP B. Surprisingly, the ligand peptides do not necessarily comprise a SH3-domain consensus binding sequence motif, like PXXP. However, the peptides of SEQUENCE LISTING GROUP B show a high content of amino acids Trp, H is, Tyr enabling additional pi-interactions with the protein MIA.

Additionally the invention covers peptides wherein one additional amino acid is present or one amino acid of the peptides is deleted.

In a further embodiment the present invention covers peptides wherein one amino acid is substituted by a natural amino acid. Natural amino acids are those 20 amino acid which usually occur in natural proteins and peptides.

Additionally one or more amino acids can be substituted by a non-natural amino acid. Such non-natural amino acid are based on natural amino acids but one or more atoms are substituted with functional groups comprising up to 50 atoms selected from C, H, N, S, O, P, F, Cl, Br, I, Se.

Examples of such non-naturally occurring amino acid residues are trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4 azaphenylalanine, and 4-fluorophenylalanine. Several methods are known in the art for incorporating non-naturally occurring amino acid residues into proteins.

In a further embodiment the peptides may be modified. Suitable modification are selected from the group consisting of glycosylation, acetylation, hydroxylation (hydroxyproline), carboxylation (gamma-carboxyglutamate), phosphorylation, alkylation, myristoylation (N-terminal), palmitoylation and prenylation. The peptides of the present invention are especially useful as medicaments, therefore, a medicament comprising at least one of the peptides of the invention also forms part of the invention.

Inhibition of MIA can also be achieved via antibody or antibody fragments. Therefore, a medicament comprising such an antibody or antibody fragment is part of the invention.

Especially useful are antibodies or antibody fragments binding to integrins according to ANTI-INTEGRIN-ANTI-BODY-LISTING, ANTIBODY NO. 1 to 4: anti-alpha4-integrin (A4-PUJ1, UBI), anti-alpha4-integrin (P1H4, Chemicon), anti-alpha5-integrin (A5-PUJ5, UBI), anti-alpha5-integrin (P1D6, Chemicon)). These antibodies or antibody fragments can be directed against alpha 4 and 5-integrins. Such antibodies are commercially available from UBI (Lake Placid, N.Y., USA) and Chemicon International, Inc. (Temecula, Calif., USA). Antibody fragments are peptides which comprise relevant parts of the antibody but are smaller in size. Suitable fragments are Fab fragments or ScFv fragments.

The peptides, antibodies or antibody fragments can be combined with agents selected from the group consisting of:
a) immunostimulatory agents: Interleukin-2 (Atkins et al., Proc Am Soc Clin Oncol. 1997; 16:494), Interferon-alpha (Rosenberg et al., 3 Clin Oncol. 1999; 17:968-975) Interferon-gamma, Interleukin-12, GM-CSF (granulocyte-macrophage colony-stimulating factor)
b) chemotherapeutic agents: Taxanes (TAXOL (Bristol-Myers Squibb), TAXOTERE (Aventis), TEMODAR (Schering-Plough)), INTRON-A (Schering-Plough), Nitrosureas, Dacarbizine, Fotemustine, Lomustine (CCNU), Anthracyclines, Vinca alkaloids (Vinblastine, Vindesine), Cisplatin (DDP) (DelPrete et al., Cancer Treat Rep. 1983; 12:1343.; Legha, et al., Cancer. 1989; 64: 2024-2029; Cocconi et al., N Eng J. Med. 1992; 327:516-523)
c) gene-therapeutic agents suitable for gene-transfer: Interleukin-7 (Schmidt-Wolf et al., Hum Gene Ther. 1994 September; 5(9):1161-8), Interleukin-2 (Stewart et al., Gene Ther 1999 March; 6(3):350-63), Interleukin-4 (Arienti et al., Hum Gene Ther 1999, Dec. 10; 10(18):2907-16), Interleukin-12 (Kang et al., Hum Gene Ther 2001 Apr. 10; 12(6):671-84), Interferon-gamma (Nemunaitis et al., Cancer Gene Ther 1999, July-August; 6(4):322-30; Fujii et al., Cancer Gene Ther 2000 September; 7(9):1220-30), GM-CSF (Kusumoto et al., Cancer Immunol Immunother 2001 September; 50(7):373-81, Loudon et al., J Gene Med 2001, September-October; 3(5):458-67), p 53 (Dummer et al., Cancer Gene Ther 2000 July; 7(7):1069-76), MHC Class I (Nabel G j et al., Proc Natl Acad Sci USA 1996 Dec. 24; 93(26):15388-93), HSV-tk (Herpes-simplex-Virus thymidinekinase) (Klatzmann et al., Hum Gene Ther 1998 Nov. 20; 9(17):2585-94; Morris et al., Gene Ther 2000 Feb. 10; 11(3):487-503), B7 (Fenton et al., Hum Gene Ther 1995 January; 6(1):87-106)
d) anti-angiogenic and/or anti-invasive agents
e) vaccines: CANCERVAX (Morton et al., Ca Cancer J Clin. 1996; 46:225-244), MELACINE, Schering-Plough/Corixa (Mitchell et al., Proc Annu Meet Am Assoc Cancer Res. 1995; 36:223)

The peptides, antibodies or antibody fragments alone or in combination with the agents mentioned above can be employed for the preparation of a drug for the prevention or the treatment of tumors.

Preferably, the peptides, antibodies or antibody fragments are applied systemically (e.g. i.v. or s.c. or orally). They may also be applied locally to a tumor or other pathologically affected site or organ. A suitable dosage is in the range from 1-50 mg/kg/day.

In a preferred embodiment for optimizing drug delivery the peptides can be encapsulated in biodegradable polymers. Such method are known to those skilled in the art. Suitable polymers include polyesters (Jeong et al., 2001, J. Pharma. Sci., 90: 10; Lewis et al., 1990, Drug Pharm. Sci. 45: 1; Wada et al., 1990, J. Pharm. Sci. 79: 919, Okada et al., 1994, J. Control. Release 28: 121, Leong et al., 1985, Biomed. Mater. Res. 19: 941; E. Ron et al., Reserve University. R. Langer, PNAS 90: 4176, 1993), polyamino acid (Anderson et al., 1979, Polymer Preprints 20; Bennet et al., 1991, J. Control. Release 16: 43), polyalkyl cynoacrylates (Couvreur et al., 1992, Adv. Drug Del. Rev. 10: 141), polyphazenes (Allcock et al., 1990, Chem. Eng. News 62: 22, Allcock et al., 1990, J. Am. Chem. Soc. 112: 783), copolymers of polylactide and aspartate (Kwon et al., 1990, J. Control. Release 11: 269), or polyethylene oxide (Youxin & Kissel, 1993, J. Control. Release 27: 243).

Further preferred are biodegradable amphiphilic microspheres (Bouillot et al., 1999, Int. J. Pharma., 181:159-172), amphipathic copolymers, such as polyoxyethylene microspheres, polyoxypropylene microspheres, human serum albumin (HSA) nanoparticles (Lin et al., 1999, Int. J. of Pharma., 185: 93-101), polylactide microspheres, polyethylene glycol (Matsumoto et al., 1999 Int. J. of Pharma., 185 (1999) 93-101), polyethylene oxide (Jeong et al., 1999 Journal of Controlled Release 62: 109-114), polyphosphazene nanoparticles (Caliceti et al., 2000, Int. J. of Pharma., 211: 57-65), and/or combinations and/or derivatives thereof.

The peptides, antibodies and antibody fragments of the invention can be used for the prevention or the treatment of diseases selected from the group consisting of:
1. Solid tumors, e.g. cancer of the skin (including melanoma), head and neck cancer, sarcoma (including osteosarcoma and chondrosarcoma), retinoblastoma, breast cancer, ovarian cancer, small-cell bronchogenic/lung carcinoma, non-small-cell bronchogenic/lung carcinoma, esophageal cancer, colon carcinoma, colorectal carcinoma, gastric cancer, small intestine carcinoma, liver carcinoma, carcinoma of the kidney, pancreas carcinoma, gallbladder cancer, cervical carcinoma, endometrial cancer, mesothelioma, prostate carcinoma, testicular carcinoma, brain tumor
2. Leukemia, e.g. myeloid leukemia (acute and chronic), acute lymphoblastic leukemia (ALL), Non-Hodgkins Lymphoma, Hodgkins-Lymphoma
3. Degenerative disorders, e.g. arthritis, degeneration/injury of cartilage and bone
4. Immunosuppressive diseases e.g. HIV infection, myelosuppressive diseases, ataxia-telangiectasia, DiGeorge syndrome, Bruton disease, congenital agammaglobulinemia, combined immunodeficiency disease, Wiscott-Aldrich syndrome, complement deficiencies, leukopenia.

The peptides, antibodies and antibody fragments of the invention can further be used for the induction and/or expansion of precursor cells (e.g mesenchymal stem cells, blood cells, chondrocytes, neurons).

Figure 1:
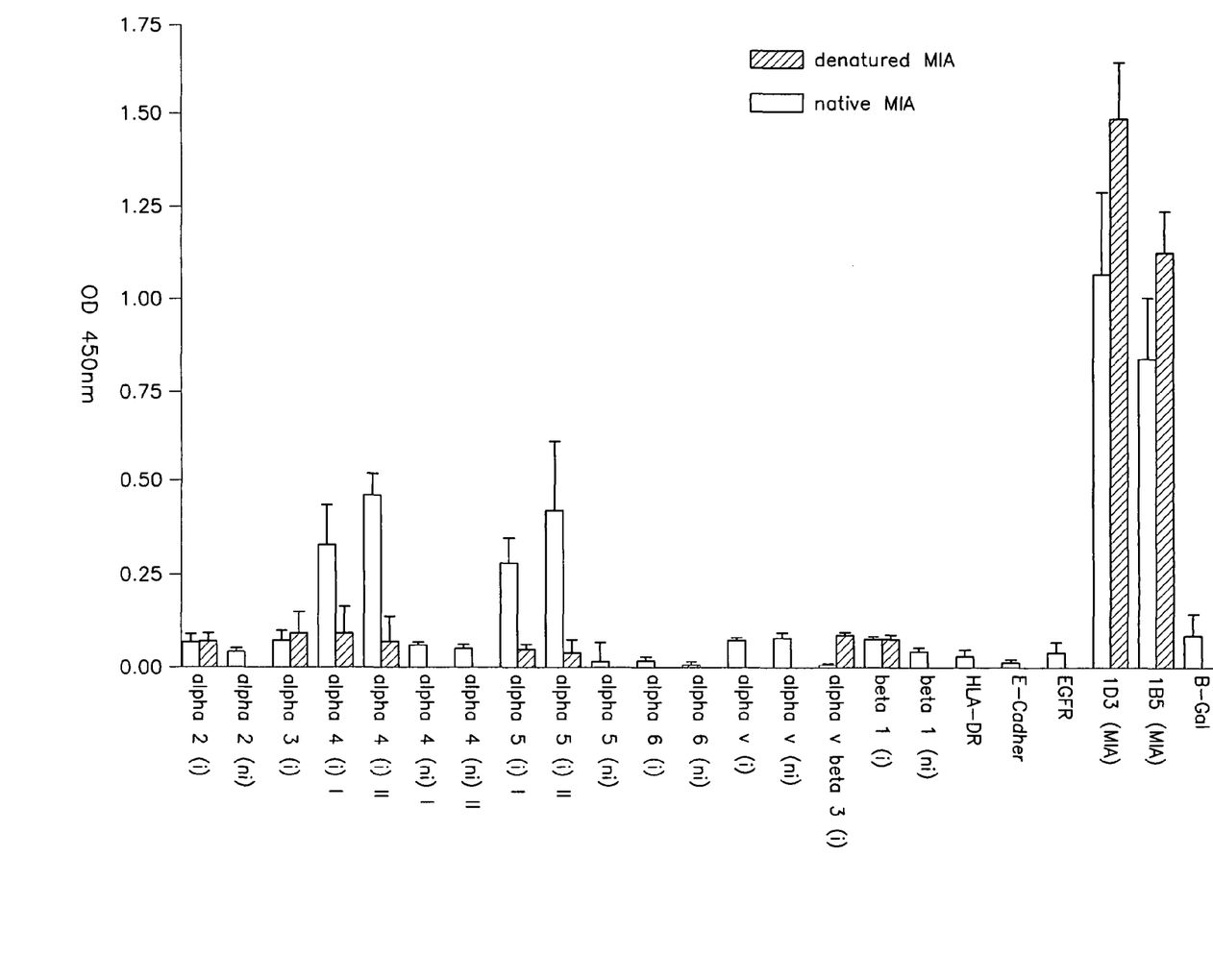
FIG. 1 graphically illustrates the specific cross-reaction of anti-alpha 4- and anti-alpha 5-integrin-inhibiting antibodies with MIA.

FIG. 1 shows the specific cross-reaction of anti-alpha 4- and anti-alpha5-integrin-inhibiting antibodies with MIA.

Bacterially purified MIA was coated to 96 well plates and incubated for 30 min. with 1 µg/ml of the following monoclonal antibodies: alpha 2-, alpha 3-, alpha 4-, alpha 5-, alpha 6-, alpha v- and beta 1-integrin inhibitory antibodies, alpha 2-, alpha 4-, alpha 5-, alpha 6-, alpha v- and beta 1-integrin non-inhibitory antibodies, HLA-DR, E-cadherin, epidermal-growth-factor receptor or beta-galactosidase antibodies and two different MIA antibodies. After washing five times with PBS/BSA binding of the respective monoclonal antibodies was detected by a horseradish peroxidase-coupled anti-mouse IgG antiserum then visualized with ABTS (Roche) and quantified after 30 min at OD405 nm.

DETAILED DESCRIPTION OF PREFERRED EMBODIMENTS

Example 1

Phage Display

Phage display screening was performed using heptapeptide and do-decapeptide phage display libraries (BioLabs, Beverly, Calif. USA) following the manufacturer's instructions. Recombinant human MIA was coated onto the wells of a high protein-binding 96-well plate at a concentration of 10 micrograms per well. Binding phages were selected by incubation in the MIA-coated plates for 60 min at room temperature. For each selection, $2 \times 10^{11}$ phages were added per well. Non-binding phages were removed by washing five times with TBS (Tris-buffered saline) for 10 min; bound phages were eluted by adding rhMIA (recombinant human MIA) at a concentration of 100 micrograms/ml. The eluted phages were amplified and the biopanning was repeated four times. The binding clones were characterized by sequencing the phage insert.

Result

Results of the phage display screening revealed a high percentage of clones carrying heptapeptides with multiple prolines. Out of 40 isolated and sequenced clones, 11 (27.5%) contained two or more prolines. Using a do-decapeptide phage display library, five sequences have been identified including the peptide SEQ-ID-NO.: 16 (pdp12) (Stoll et al. 2001; EMBO J. 20: 340-349, Table II).

Example 2

MIA Immunoassay

MIA was coated to 96-well plates and incubated for 30 minutes with 1 microgram/ml of the following monoclonal antibodies: Anti-alpha2-integrin (P1E6, DAKO, Hamburg, Germany), anti-alpha2-integrin (A2-11E10, UBI, Lake Placid, N.Y., USA), anti-alpha3-integrin (P1B5, DAKO, Hamburg, Germany), anti-alpha4-integrin (A4-PUJ1, UBI, Lake Placid, N.Y., USA), anti-alpha4-integrin (B-5G10, UBI, Lake Placid, N.Y., USA), anti-alpha4-integrin (P4C2, Chemicon), anti-alpha4-integrin (P1H4, Chemicon), anti-alpha4-integrin (AB1924, Chemicon), anti-alpha5-integrin (A5-PUJ5, UBI, Lake Placid, N.Y., USA), anti-alpha5-integrin (P1D6, Chemicon), anti-alpha5-integrin (AB1949, Chemicon), anti-alpha6-integrin (A6-ELE, UBI, Lake Placid, N.Y., USA), anti-alpha6-integrin (provided by Dr. E. Klein, Würzburg), anti-alpha-v-integrin (P3G8, Chemicon), anti-alpha-v-integrin (AB1930, Chemicon), anti-alpha-v-beta 3-integrin (Lv 230), anti-alpha-v beta 3-integrin (LM609, Chemicon), anti-beta 1-integrin (6S6, Chemicon), anti-beta 1-integrin (AB1952, Chemicon), anti-HLA-DR-(CR3743, DAKO, Hamburg, Germany), anti-E-cadherin-(MLCA, EuroDiagnostica, Germany) and anti-EGF-receptor-antibody (Clone F4, Sigma, Deisenhofen, Germany) and two different anti-MIA antibodies (Dr. B. Kaluza, Roche). After washing five times with PBS (phosphate buffered saline)/3% BSA (bovine serum albumine), binding of the respective monoclonal antibody was detected by a horseradish peroxidase-coupled anti-mouse IgG antiserum, then visualized with ABTS (2.2 '-azino-di-(3-ethylbenzthiazolin-sulfonat)) (Roche) and quantified at O.D. 405 nm after 30 minutes. As a control for specificity denatured MIA was used performing the same kind of assay.

Results

Surprisingly, all peptides/proteins that bind to MIA serve as binding sites for certain integrins raising the possibility that MIA and the ligand binding pockets of these integrins share three-dimensional homology. Addressing this possibility we asked whether monoclonal antibodies that inactivate the binding pockets of integrins (Hemler, et al., 1987 J. Biol. Chem. 262, 11478-11485) cross-react with MIA. In parallel controls were performed with anti-integrin antibodies recognizing epitopes outside the binding pocket (Bergelson, et al., 1992, Science 255, 1718-1720; Teixido, et al., 1992, J. Biol. Chem. 267, 1786-1791; Falcioni, et al., 1986, Cancer Res. 46, 5772-5778) and with antibodies recognizing cell surface epitopes other than integrins (E-Cad, EGF-Rec and HLA-DR). Positive control reactions were performed with two monoclonal anti-MIA antibodies. Results from these immunoreactions revealed that the four antibodies that inactivate the binding pockets of alpha 4- and alpha 5-integrins (anti-alpha 4-integrin (A4-PUJ1, UBI), anti-alpha4-integrin (P1H4, Chemicon), anti-alpha5-integrin (A5-PUJ5, UBI) and anti-alpha5-integrin (P1D6, Chemicon)) cross-react specifically with MIA in contrast to all other integrin and cell surface molecule antibodies (submitted for publication 2002;

Bosserhoff et al.), see FIG. 1. These results suggest strongly that the activated binding pockets of alpha 4 beta 1- and alpha 5 beta 1-integrin receptors share significant three-dimensional homology with MIA.

To demonstrate the importance of the three-dimensional structure and correct folding of the MIA protein, the same assay was repeated using reduced MIA protein. As it is known that the two cystine bonds are essential for MIA folding, reducing conditions lead to denaturing of the protein. All antibodies that cross-reacted with native MIA were incapable to bind to denatured MIA protein. Further, western-blot analysis was performed using the same panel of anti-integrin antibodies. Again, none of the antibodies detecting native MIA protein reacted with MIA under reducing conditions (submitted for publication 2002; Bosserhoff et al.).

Example 3

In Vivo Metastasis Assay

To measure the effect of SEQ ID NO: 16 and SEQ ID NO:22 on the metastatic potential of B16 melanoma cells in vivo an experimental metastasis assay was used (Bosserhoff et al., 2001, Melanoma Res. 11, 417-421). Intravenous injections of monodispersed tumor cells ($1 \times 10^5$ cells per animal) were performed into syngeneic C57BI6 mice (n=12 for every peptide as well as control). Peptides (550 µg/mouse) or PBS was injected every day. After 18 days the mice were sacrificed, the lungs removed, washed in PBS, fixed in formalin and the visible tumor nodules on the surface of the lungs were counted and the tumor areas measured.

Results

Both in vitro and in vivo MIA expression levels strictly correlate with an highly invasive phenotype (Bosserhoff et al., 1996, J. Biol. Chem. 271, 490-495; Bosserhoff et al., 1999, J. of Pathology 187, 446-454). Further in vivo studies have shown the necessity of MIA for melanoma invasion and metastasis (Bosserhoff et al., 2001, Melanoma Res. 11, 417-421., Guba, et al., 2000, Br. J. Cancer 83, 1216-1222). We therefore aimed to design MIA-inhibitory peptides based on our experiments which identified fibronectin epitopes interacting with MIA (Stoll et al., 2001; EMBO J. 20: 340-349). Peptides derived from fibronectin which were shown previously to cross-react with MIA were tested in Boyden Chamber assays on their effect on melanoma cell invasion with and without MIA. The results clearly reveal that the peptides SEQ ID NO:22, 23, and 24 block MIA function and further that SEQ ID NO:23 and 24 inhibit also tumor cell attachment. In addition we tested several of the peptide sequences derived from phage display screenings and found peptide SEQ ID NO:16 to be a potential interesting candidate for therapeutic MIA-inhibition. It showed no effect on melanoma cell attachment but strongly inhibited MIA function. We then tested the effect of peptides SEQ ID NO:16 and 22 on growth of metastasis in vivo using the B16/C57B16 model. The number of black lung nodules of melanoma was not significantly changed between treated and untreated control (193±13 (control); 249±26 (SEQ ID NO:22); 198±19 (SEQ ID NO:16)). However, significant changes were seen in the size of the nodules. Animals treated with the peptides developed significantly smaller tumor nodules compared to the control animals (119.9±9.95 (control); 87.15±5.32, p=0.0042 (SEQ ID NO:22); 78.1±5.03, p=0.0003 (SEQ ID NO:16)).

Example 4

Expression and Purification of Recombinant MIA Protein

*Escherichia coli* M15 (pREP4) cells transfected with the expression plasmid pQE40-MIA expressing 108 residues of human MIA (G25 to Q131) were grown to an absorbance $O.D._{600\,nm}=0.6$, induced by 1 mM isopropyl-1-thio-_-D-galactopyranoside for 4 hours and lysed by sonication. The protein was renatured from *E. coli* inclusion bodies as previously published (Jaenicke, R. & Rudolph, R. (1986) Methods Enzymol. 131:218-50, 218-250). Refolded human MIA was applied to hydrophobic interaction chromatography and further purified on a S-SEPHAROSE Fast Flow (high molecular weight gel) (Sigma). Finally, gel filtration was performed on a SUPERDEX200 Prep Grade (gel filtration material) (Sigma). Fractions containing human MIA were pooled and concentrated. Purified protein was checked by SDS-Page and HPLC and was shown to be 95% pure.

Example 5

Docking of Peptides to the Protein Crystal Structure of MIA

For virtual docking of the peptides to the protein MIA the peptide sequences SEQ ID No:1-55 and the crystal structure with pdb code 1I1J (Lougheed et al., 2001, PNAS USA 98, 5515-5520) have been used. Both peptides and protein have been ionized using the molecular graphics suite SYBYL (Tripos Inc., St. Louis, USA). The binding site of the protein MIA has been defined applying the protein amino acids Leu27, Gln28, Asp29, Tyr30, Ala32, Arg42, Leu52, Arg57, Leu58, Phe59, Gly57, Tyr78, Phe79, Pro80, Ser81, Ser82, Ile83, and Arg85. The docking was performed using the program 4Scan (4SC GmbH, Martinsried, Germany). For each peptide ligand the binding energy and the amino acids of both peptide ligand and protein involved in binding have been analyzed. The peptide ligands have been ranked by binding energy.

Results

Surprisingly, the ligand peptides SEQ ID No:1-57 do not necessarily comprise a SH3-domain consensus binding sequence motif, like PXXP.

In contrast to results published earlier, the amino acid sequence motif (ligand) involved in binding to the MIA protein can be defined as "inter-proline sequence motif" with at least one proline amino acid residue in SEQ ID NO:01-11, SEQ ID NO:13-20, SEQ ID NO:22-31, SEQ ID NO:35-36. SEQ ID NO:38, SEQ ID NO:40-44, SEQ ID NO:46-49, SEQ ID NO:51-57.

Based on the virtual docking of the peptides SEQ ID No: 1-55 onto the protein crystal structure of MIA (Code 1I1J; Lougheed, et al., 2001, Proc. Natl. Acad. Sci. USA 98, 5515-5520), both the functional role of the "inter-proline sequence motif" and the binding site of the peptides can be identified.

All the peptides, besides SEQ ID No:22, 43, 48 are bound over their entire length and interact with MIA by both hydrogen-bonding and van der Waals contacts. The proline amino acid residues (ligand) are involved in reaching these extreme inter-peptide torsion angles and thereby supporting the binding of the ligand. The prolines are mainly involved in van der Waals complex interactions and not in hydrogen-bonds.

The peptides preferably bind to the three amino acid residues Arg42, Asp29, and Gln28 (human MIA), at the surface of the protein. Binding to this "MIA-binding triad" enforces kinks in the stereogeometry of the ligand. Surprisingly, the residue Arg42 (MIA) is not conserved within the SH3-protein family.

The peptides of SEQ GROUP A (SEQ ID NO:1-24) consist of a higher content of proline (22.4%) compared to SEQ GROUP B (12.0%), therefore showing higher stereogeometric flexibility for binding to the protein.

Peptides of SEQ GROUP B (SEQ ID NO:25-57) compensate this by a higher content of the amino acids Trp, His, and Tyr. Binding of the peptides of SEQ GROUP B (SEQ ID NO:25-57) to the MIA-binding triad described above is enforced by pi-interactions of amino acid residue Tyr30 (MIA) to these amino acid side chains (ligand). Peptides of SEQ GROUP B (SEQ ID NO:25-57) contain 8.5% Trp, 7.9% His, and 3.0% Tyr (GROUP A: 2.5% Trp, 3.8% His, 0.8% Tyr).

Both peptides groups SEQ GROUP A and B of the invention consist of a high content of Leu (11%), Ser (10%), and Thr (9%).

Sequence Listing

The inhibition of the function of MIA is preferably achieved by using molecules comprising the following amino acid sequences:

| SEQUENCE LISTING GROUP: A | |
|---|---|
| SEQ ID NO: 01 | VPHIPPN |
| SEQ ID NO: 02 | MPPTQVS |
| SEQ ID NO: 03 | QMHPWPP |
| SEQ ID NO: 04 | QPPFWQF |
| SEQ ID NO: 05 | TPPQGLA |
| SEQ ID NO: 06 | IPPYNTL |
| SEQ ID NO: 07 | AVRPAPL |
| SEQ ID NO: 08 | GAKPHPQ |
| SEQ ID NO: 09 | QQLSPLP |
| SEQ ID NO: 10 | GPPPSPV |
| SEQ ID NO: 11 | LPLTPLP |
| SEQ ID NO: 12 | QLNVNHQARADQ |
| SEQ ID NO: 13 | TSASTRPELHYP |
| SEQ ID NO: 14 | TFLPHQMHPWPP |
| SEQ ID NO: 15 | VPHIPPNSMALT |
| SEQ ID NO: 16 | RLTLLVLIMPAP |
| SEQ ID NO: 17 | RKLPPRPRR |
| SEQ ID NO: 18 | VLASQIATTPSP |
| SEQ ID NO: 19 | TPLTKLPSVNHP |
| SEQ ID NO: 20 | PPNSFSSAGGQRT |
| SEQ ID NO: 21 | EQDSRQGQELTKKGL |
| SEQ ID NO: 22 | ETTIVITWTPAPR |
| SEQ ID NO: 23 | TSLLISWDAPAVT |
| SEQ ID NO: 24 | NSLLVSWQPPRAR |

SEQ ID NO:01 to SEQ ID NO:24 refer to peptides published by Stoll et al., 2001, EMBO J. 20: 340-349, wherein the SEQ ID NO:01 to SEQ ID NO:16 were obtained by phage-display.

SEQ ID NO:17 to SEQ ID NO:24 are other peptides tested in this study, including control peptides (SEQ ID NO:20 and SEQ ID NO:21), a PI3-kinase SH3 domain binding peptide (SEQ ID NO:17) and fibronectin-derived peptides (SEQ ID NO:22 to SEQ ID NO:24).

| SEQUENCE LISTING GROUP: B | |
|---|---|
| SEQ ID NO: 25 | YNLPKVSSNLSP |
| SEQ ID NO: 26 | MPPTQVSKFRLI |
| SEQ ID NO: 27 | ANIDATPLFLRA |
| SEQ ID NO: 28 | LLRTTETLPMFL |
| SEQ ID NO: 29 | SALEPLV |
| SEQ ID NO: 30 | GSPTPNA |
| SEQ ID NO: 31 | APSHATH |
| SEQ ID NO: 32 | TTVGHSD |
| SEQ ID NO: 33 | THFSTFT |
| SEQ ID NO: 34 | SLLLDTS |
| SEQ ID NO: 35 | SVAMKAHKPLLP |
| SEQ ID NO: 36 | NTIPGFASKSLD |
| SEQ ID NO: 37 | VSNYKFYSTTSS |
| SEQ ID NO: 38 | VSRHQSWHPHDL |
| SEQ ID NO: 39 | HLNILSTLWKYR |
| SEQ ID NO: 40 | HNASPSWGSPVM |
| SEQ ID NO: 41 | SHPWNAQRELSV |
| SEQ ID NO: 42 | HHWPFWRTLPLS |
| SEQ ID NO: 43 | WHTKFLPRYLPS |
| SEQ ID NO: 44 | NNTSFTVVPSVP |
| SEQ ID NO: 45 | SHLSTWKWWQNR |
| SEQ ID NO: 46 | FHWHPRLWPLPS |
| SEQ ID NO: 47 | WHWTYGWRPPAM |
| SEQ ID NO: 48 | FHWRYPLPLPGQ |
| SEQ ID NO: 49 | WHWPLFIPNTTA |
| SEQ ID NO: 50 | WHNGIWWHYGVR |
| SEQ ID NO: 51 | HHLNYLWPWTRV |
| SEQ ID NO: 52 | FWHRWSTFPEQP |
| SEQ ID NO: 53 | WHMSYFWTRPPQ |
| SEQ ID NO: 54 | FHLNWPSRADYL |
| SEQ ID NO: 55 | WHKNTNWPWRTL |
| SEQ ID NO: 56 | ALSPSQSHPVRS |
| SEQ ID NO: 57 | GTQSTAIPAPTD |

SEQ ID NO:25 to SEQ ID:NO 57 were obtained by phage-display.

Anti-Integrin-Antibody Listing

The inhibition of the function of MIA is also preferred to be achieved by the use of the following inactivating anti-alpha 4- and anti-alpha5-Integrin-antibodies:

ANTIBODY NO. 1: anti-alpha4-integrin (A4-PUJ1, UBI)
ANTIBODY NO. 2: anti-alpha4-integrin (P1H4, Chemicon)
ANTIBODY NO. 3: anti-alpha5-integrin (A5-PUJ5, UBI)
ANTIBODY NO. 4: anti-alpha5-integrin (P1D6, Chemicon)

The invention claimed is:

1. An isolated peptide consisting of the amino acid sequence of SEQ ID NO: 48 modified by glycosylation, acetylation, hydroxylation, carboxylation, phosphorylation, alkylation, myristoylation, palmitoylation, or prenylation, wherein the peptide specifically binds a MIA polypeptide comprising the amino acid sequence of SEQ ID NO: 58.

2. An isolated peptide consisting of the amino acid sequence of SEQ ID NO: 48 but for the substitution of one amino acid by a natural or non-natural amino acid, wherein the peptide specifically binds a MIA polypeptide comprising the amino acid sequence of SEQ ID NO: 58.

3. The isolated peptide of claim 2, wherein the substitution of one amino acid is by a non-natural amino acid is selected from the group consisting of trans-3-methylproline, 2,4-methanoproline, cis-4-hydroxyproline, trans-4-hydroxyproline, N-methylglycine, allothreonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine.

4. An isolated peptide consisting of the amino acid sequence of SEQ ID NO: 48 but for the addition of one amino acid at either end, wherein the peptide specifically binds a MIA polypeptide comprising the amino acid sequence of SEQ ID NO: 58.

5. An isolated peptide consisting of the amino acid sequence SEQ ID NO: 48 but for the deletion of one amino acid, wherein the peptide specifically binds a MIA polypeptide comprising the amino acid sequence of SEQ ID NO: 58.

6. A composition comprising the peptide according to claim 1 in combination with an acceptable biodegradable polymer.

7. A composition comprising the peptide according to claim 2 in combination with an acceptable biodegradable polymer.

8. A composition comprising the peptide according to claim 3 in combination with an acceptable biodegradable polymer.

9. A composition comprising the peptide according to claim 4 in combination with an acceptable biodegradable polymer.

10. A composition comprising the peptide according to claim 5 in combination with an biodegradable polymer.

* * * * *